United States Patent [19]

Babchin et al.

[11] Patent Number: 5,293,773

[45] Date of Patent: Mar. 15, 1994

[54] METHOD FOR DETERMINING THE WETTING PREFERENCE OF PARTICULATE SOLIDS IN A MULTIPHASE LIQUID SYSTEM

[76] Inventors: Alexander J. Babchin, Suite 202, 10160 - 115 Street, Edmonton, Alberta, Canada, T5K 1T6; Haibo Huang, 310 Cumberland Avenue East, Saskatoon, Saskatchewan, Canada, S7N 1M5; Kevin Rispler, 189 Callingwood Place, Edmonton, Alberta, Canada, T5T 2C6; William D. Gunter, 11239 - 63 Street, Edmonton, Alberta, Canada, T5W 4E5

[21] Appl. No.: 880,447

[22] Filed: May 8, 1992

[30] Foreign Application Priority Data

May 9, 1991 [GB] United Kingdom ............... 9109995

[51] Int. Cl.$^5$ ..................... G01N 13/02; G01N 29/00
[52] U.S. Cl. .................. 73/64.48; 73/53.01; 73/64.53; 73/606
[58] Field of Search ................. 73/64.48, 64.53, 606, 73/865.5, 53.01; 324/663

[56] References Cited

U.S. PATENT DOCUMENTS

| | | | |
|---|---|---|---|
| 4,294,656 | 10/1981 | Beck et al. | 162/192 |
| 4,497,208 | 2/1985 | Oja et al. | 73/584 |
| 4,552,019 | 11/1985 | Freeman | 73/584 |

OTHER PUBLICATIONS

A. J. Babchin; "Electrokinetic Measurements by Electroacoustical Methods", Advances in Colloid & Interface Science, 30(1989), pp. 111–151.

William G. Anderson, "Wettability Literature Survey-Part 2: Wettability Measurement," Nov. 1986, Journal of Petroleum Technology, pp. 1246–1262.

*Primary Examiner*—Robert J. Warden
*Assistant Examiner*—L. M. Crawford
*Attorney, Agent, or Firm*—Falk, Vestal & Fish

[57] ABSTRACT

A method is provided for determining the wetting preference of particulate solids, for example sand, dispersed in a multiphase liquid medium having a continuous phase and a discontinuous phase, for example a water-in-oil emulsion. A dispersion of the particulate solids and the liquid medium is passed through an electroacoustical cell and the electroacoustical signal is measured for varying solids content. If the signal remains substantially constant this indicates a wetting preference for the continuous phase, whereas if the signal decreases this indicates a wetting preference for the discontinuous phase.

4 Claims, 1 Drawing Sheet

METHOD FOR DETERMINING THE WETTING PREFERENCE OF PARTICULATE SOLIDS IN A MULTIPHASE LIQUID SYSTEM

BACKGROUND OF THE INVENTION

In studying oil recovery processes, cores are often used in order to predict the behaviour of the reservoir to a particular recovery technique. An important reservoir property to be duplicated in the core is the wettability or wetting preference of the reservoir solids. Changes in the wettability of the core have been shown to affect electrical properties, capillary pressure, water-flood behaviour, relative permeability, dispersion and simulated enhanced oil recovery. In order for the core analysis to predict the behaviour of the reservoir, the wettability of the core must be the same as the wettability of the undisturbed reservoir rook.

There are several methods, quantitative and qualitative, for measuring wettability of a reservoir core. Three quantitative measurements are most often used: (1) contact - angle measurement, (2) the Amott method (involving imbibition and forced displacement), and (3) the U.S. Bureau Mines method. These methods and others are described and compared in W.G. Anderson, "Wettability Literature Survey", J. of Petroleum Technology", 1246 (1986). Such wettability or wetting preference measurements typically provide an indication of whether the solid surface is preferentially oil-wet or preferentially water-wet.

Generally speaking, the above techniques are best suited to measuring the wettability of a consolidated surface or a consolidated core. No method, to the inventors' knowledge, exists for measuring the wettability of a dispersed medium, i.e. particulate solids dispersed in a multiphase liquid medium such as oil and water.

Electroacoustical methods and apparatus are known for measuring the electro-kinetical properties of liquids, colloidal suspensions or slurries, see for example U.S. Pat. No. 4,294,696 issued Oct. 13, 1981 to Beck et al.; U.S. Pat. No. 4,497,208 issued Feb. 5, 1985 to Oja et al.; U.S. Pat. No. 4,552,019 issued Nov. 12, 1985 to Freeman; and A.J. Babchin et al., "Elecotrokinetic Measurements by Electroacoustical Methods", Adv. Colloid Interface Sci., 30, 111 (1989). These references disclose techniques to measure electroacoustical signals proportional to electrokinetic potentials of dispersed particles etc. (i.e. signals Which correlate sonic and electrical fields). However, electrokinetic potentials are only very weakly related to wetting properties of solids. Therefore, no conclusions on wetting properties can be made on the basis of a direct measurement electrokinetic potential.

SUMMARY OF THE INVENTION

The inventors have discovered that standard electroacoustical instruments can be used to determine the wettability or wetting preference of particulate solids dispersed in a multiphase liquid medium. The inventors demonstrated, in respect of water-in-oil emulsions, that particulate solids known to have a wetting preference to oil (i.e. hydrophobic particles such as latex particles), when added to the emulsion do not significantly affect the magnitude of the electroacoustical signal, regardless of the solids content. However, when particulate solids known to have a wetting preference to water (i.e. hydrophillic particles such as sand particles) were added to the emulsion, it was shown that the electroacoustical signal was reduced proportional to the mass of the particulate solids added to the emulsion.

Broadly, the invention provides a method for determining the wetting preference of particulate solids dispersed in a multiphase liquid medium having a continuous and a discontinuous phase. The method comprises (a) dispersing the particulate solids in multiphase liquid at varying solids contents, (b) passing the dispersion through an electroacoustical cell, (c) measuring the electroacoustical signal of the dispersion with varying solids contents, and (d) determining whether the signal remains substantially constant or decreases with increasing solids content, the former indicating that the particulate solids have a wetting preference for the continuous phase, the latter indicating that the solids have a wetting preference for the discontinuance phase.

Without being bound by the same, the theory behind the method is believed to be as follows. In the above-mentioned reference by Babchin et al. certain relationships were set out in respect of electroacoustical measurements of colloidal systems. For the same volume concentration of a dispersed phase, the electroacoustical signal is proportional to the high frequency electrophoretic mobility $\mu(\omega)$ of particles or drops in the dispersion. The following relationship exists for the value of the high frequency electrophoretic mobility of spherical rigid particles for small potentials:

$$\mu(\omega) = \frac{\epsilon \zeta f(\kappa R)}{\sqrt{(6\pi \eta \bar{R})^2 + \left[\frac{4}{3} \omega \pi \rho_{eff} R^2\right]^2}} \quad (1)$$

wherein:

$$\bar{R} = 1 + \frac{R}{\delta} \quad (2)$$

$$\delta = (2\eta/\rho\omega)^{\frac{1}{2}} \quad (3)$$

$$\rho_{eff} = \rho_o + \frac{9}{4R} \sqrt{\frac{2\eta\rho}{\omega}} \left(1 + \frac{2R}{9\delta}\right) \quad (4)$$

wherein:
$\epsilon$ is the dielectric permeability of the continuous phase,
$\zeta$ is the electrokinetic potential,
$f(\kappa R)$ is the dynamic Henry function,
$\eta$ is the dynamic viscosity,
$\rho$ is the density of the liquid phase,
$R$ is the particle radius, and
$\omega$ is the frequency.

From the above relationships, it was noted that an increase in the effective particle radius, which is the case in coagulation processes, leads to a decrease in $\mu(\omega)$, and consequently a decrease in the electroacoustical signal.

The mobility, $\mu$, in non-alternating fields which can be expresses by the Henry formula:

$$\mu = \frac{\epsilon \zeta}{6\pi\eta} f(\kappa R) \quad (5)$$

as the static mobility and in alternating fields as the dynamic mobility, $\mu(\omega)$, the ration of dynamic to static mobility can be given by the formula (for non-polar continuous media):

$$\frac{\mu(\omega)}{\mu} = \frac{6\pi\eta}{\sqrt{(6\pi\eta\bar{R})^2 + \left[\frac{4}{3}\pi\omega\rho_{eff}R^2\right]}} \quad (6)$$

the calculated ratio of dynamic to static mobility for a test frequency of 1.0 MHz is represented in Table 1 for a broad range of particle sizes.

TABLE 1

The Calculated Ratio of Dynamic to Static Mobility

| Particle Radius, $\mu m$ | Dynamic/Static Mobility |
| --- | --- |
| 0.05 | 0.918 |
| 1.05 | 0.324 |
| 5.05 | 0.049 |
| 10.05 | 0.015 |

[1]calculated for latex particle suspended in water at 25 C and a test frequency of 1.0 MHz.

From this table, it can be seen that particles size has a strong effect on electroacoustical signals. From this relationship, the inventors deduced that, if the radius of the dispersed solid particles significantly exceeded the radius of the emulsion drops, solid particles would not contribute significantly to the total electroacoustical signal due to an inertial effect.

DESCRIPTION OF THE PREFERRED EMBODIMENT

Figure 1:
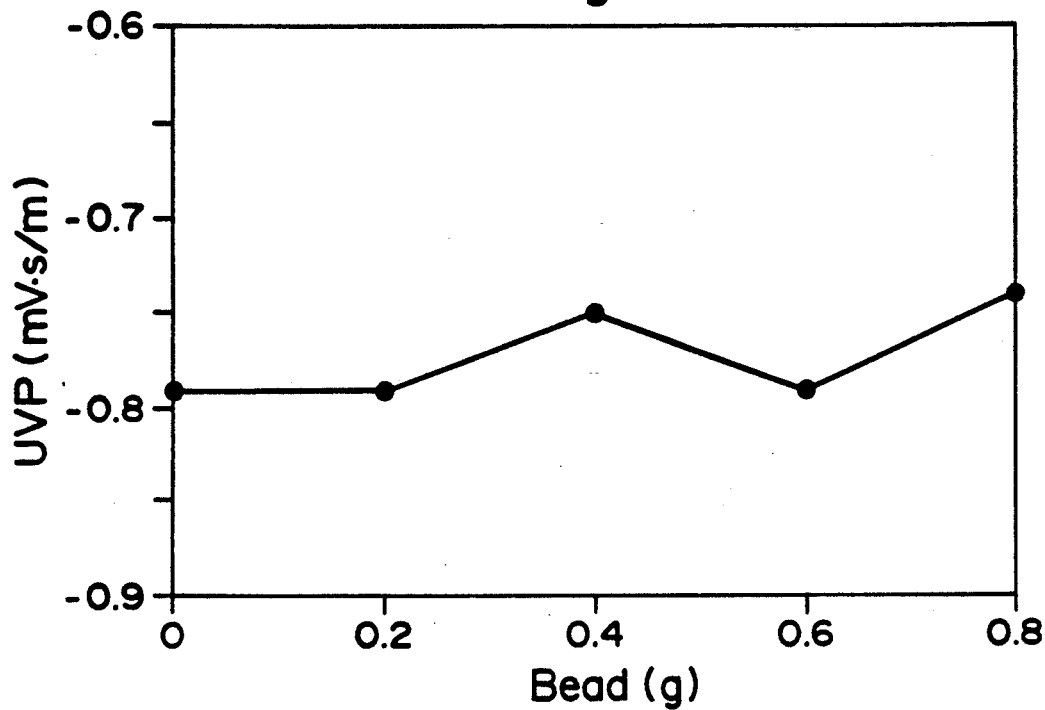
FIG. 1 is a plot showing the electroacoustical signal (ultrasonic vibrational potential) as a function of amount of solids for a dispersion of polystyrene in a water-in-oil emulsion.

In accordance with the present invention, when electroacoustical signals are used to determine the wetting preference of particulate solids dispersed in a multiphase liquid medium (i.e. an emulsion of two or more immiscible liquids) having a continuous phase and a discontinuous phase (such as oil and water), two extremes exist:

1) Wettability of the particulate solids to the continuous phase (e.g. oil in a water-in-oil emulsion) is preferential, in which case, the volume concentration of the solid phase (up to a concentration of about 5% by volume, at which point a significant sound attenuation effect is observed) is found not to affect, or affects only insignificantly, the measured electroacoustical signal (e.g. measured as the ultrasonic vibrational potential (UVP)).

2) Wettability of the particulate solids to the discontinuous phase (e.g. emulsion water in a water-in-oil emulsion) is preferential, in which case part of the dispersed liquid will envelope the particulate solids, forming new larger mechanical units. Due to inertial effects, as predicted above, this new unit of particulate solid and liquid envelope does not contribute to the electroacoustical signal. However, the total volume concentration of the remaining free liquid droplets in the multiphase liquid medium decreases by an amount dependent on the concentration of the solid phase. Therefore, the total electroacoustical signal decreases because of the signal dependence on the concentration of the solid phase. Thus, if samples of the dispersion with increasing solids content are passed through the electroacoustical cell, the measured electroacoustical signal, (e.g. UVP) decreases, indicating a wetting preference for the discontinuous phase. A plot of electroacoustical potential against the solids content shows a linear relationship. The slope of the plot is characteristic of the wetting preference of the particular solid dispersion.

Electroacoustical apparatus and methods of operation are known, see for example, the above-mentioned references, which describe measurement of UVP (ultrasonic vibration potential) and ESA (electrokinetic sonic amplitude). In the method of this invention, the solids content is preferably kept below about 5% by volume, to avoid causing a sound attenuation effect. The electroacoustical measurement is preferably obtained by measuring the UVP while pumping the sample dispersion (with varying amounts of particulate solids) through the electroacoustical cell.

EXAMPLE

This example illustrates the process of the present invention with dispersed solids in a multiphase liquid medium. Sand and polystyrene beads were used as the hydrophillic and the hydrophobic solids in a water-in-oil emulsion system. The process is equally applicable to oil-in-water emulsions. Varying quantities of each of the solids (38 to 45 $\mu m$ particle size) were dispersed in a 10% water-in-oil emulsion and the resulting UVP was measured as dispersions of different solids content were pumped through the electroacoustical cell of an electroacoustical instrument. In greater detail:

Apparatus

1. Metec Instrument ESA system coupled with a PPL-80 electroacoustical probe (obtained from Matec Applied Sciences Inc., Hopkinton Mass. U.S.A.).

2. Cole—Parmer Masterflex peristaltic pump (obtained from Cole—Parmer Instrument Co., Chicago, Ill. U.S.A.) plumbed with Tygon R-3603 tubing (¼"ID×7/16"OD).

3. Fisher Sonic Dismembrator 300 with medium immersion tip.

4. Magnetic stirrers, balance, muffle furnace, sieving equipment, glassware.

Materials

1. Crude oil from Leduc, Alberta field.
2. Sand—natural, sieved to 38–45 $\mu m$ fraction, ignited at 550 C. for 8 hours to remove organics.
3. Polystyrene beads—0.5% divinylbenzene, sieved to 38–45 $\mu m$ fraction.
4. Potassium chloride—0.01M solution
5. Toluene, deionized water.

Procedure

Instrument Set Up:

The equipment was warmed up for 30 minutes, following which a test run was performed using the 0.01M KCl solution. Once a bubble free volume of solution was being pumped through the cell, the UVP measurement was found to be 0.14 mVs/m. When conducting measurements, both the inlet and outlet tubes of the electroacoustical cell are placed in a beaker to allow for circulation of the sample. The pump was cleaned with toluene, then hot water and then deionized water.

Sand Preparation:

Varying quantities of sand (0.5, 1.0, 1.5 and 2.0 g) were dried at 120 C. for 30 minutes. The dried quantity of sand was then stirred into 10 ml of deionized water and stirred for 10 min. Crude oil (90 ml) was then added and the mixture stirred for 10 min. The mixture was again dispersed prior to measurement by stirring for 5 min and then subjecting to 5 min of ultrasound with the dismembrator. The emulsion was then pumped through the electroacoustical cell and three consecutive UVP measurements were taken for each sample of varying sand content. A control sample without the sand was also prepared and measured.

Polystyrene bead preparation:

Because of the difference between the two solids (sand density 2.6 vs. polystyrene density 1.05), the amount of polystyrene used was corrected to obtain similar conditions. Thus, the quantities used were 0.2, 0.4, 0.6, and 0.8 g. No bead drying was conducted. Otherwise the sample preparation and measurement was the same as for the sand samples, except water was titrated to pH=3.

Figure 2:
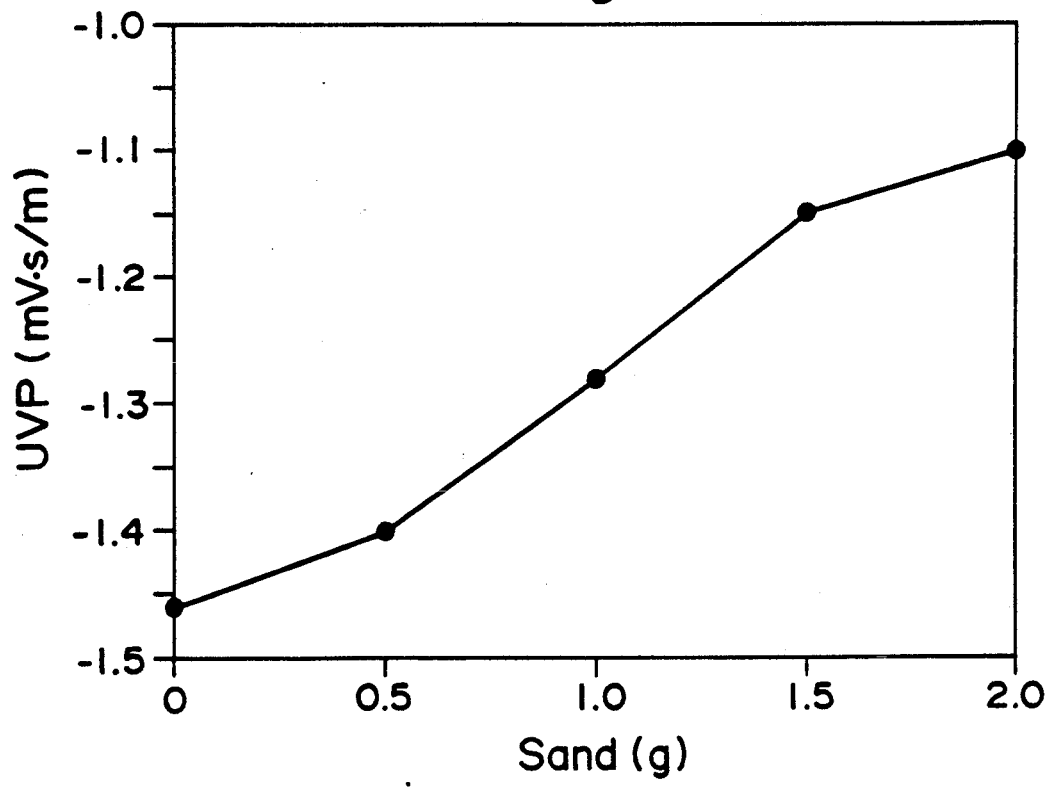
FIG. 2 is a plot similar to FIG. 1 for a dispersion of sand in a water-in-oil emulsion.

The results are shown in FIGS. 1 and 2 for polystyrene beads and sand respectively. The plots show UVP measurement vs. amount of solid. For polystyrene, the UVP measurement stayed substantially constant with increasing solid content indicating an oil-wet preference. For sand, the UVP decreased substantially with increasing sand content, indicating a water-wet preference.

When the same sand was first pre-wetted with oil and then dispersed in a water-in-oil emulsion (as set out above), the UVP measurements were found to remain substantially constant (as had been the case for the polystyrene beads) indicating that the pre-wetted sand appeared to be oil-wet. These experiments were repeated several times and the results were stable.

The terms and expressions used in this specification are used as terms of description and not of limitation. There is no intention, in using such terms and expressions, of excluding equivalents of the features shown and described, it being recognized that the scope of the invention is defined and limited only by the claims which follow.

We claim:

1. A method for determining the wetting preference of particulate solids dispersed in a multiphase liquid medium having a continuous phase and a discontinuous phase, comprising:
    (a) dispersing particulate solids in a multiphase liquid medium at varying solid contents;
    (b) passing the dispersion through an electroacoustical cell;
    (c) measuring an electroacoustical signal of the dispersion with varying solids content; and
    (d) determining whether the signal remains substantially constant or decreases with increasing solids content, the former indicating that the particulate solids have a wetting preference for the continuous phase, the latter indicating that the solids have a wetting preference for the discontinuous phase.

2. The method of claim 1, wherein the electroacoustical signal measured is the ultrasonic vibrational potential (UVP).

3. The method of claim 2, wherein the continuous phase is oil, the discontinuous phase is water and the multiphase liquid medium is a water-in-oil emulsion.

4. The method of claim 3, wherein the particulate solids are sand or mineral particles and are included in an amount less than about 5% volume.

* * * * *